(12) United States Patent
Shloznikov

(10) Patent No.: US 6,546,290 B1
(45) Date of Patent: Apr. 8, 2003

(54) METHOD AND APPARATUS FOR ELECTROMEDICAL THERAPY

(75) Inventor: Boris Shloznikov, Toronto (CA)

(73) Assignee: Roamitron Holding S.A., Luxembourg (LU)

( * ) Notice: Subject to any disclaimer, the term of this patent is extended or adjusted under 35 U.S.C. 154(b) by 0 days.

(21) Appl. No.: 09/548,375

(22) Filed: Apr. 12, 2000

(51) Int. Cl.$^7$ .................................................. A61N 1/18
(52) U.S. Cl. .......................... 607/48; 607/46; 607/115
(58) Field of Search .............................. 607/76, 72, 74, 607/115, 148, 152, 46, 48, 140

(56) References Cited

U.S. PATENT DOCUMENTS

| | | | |
|---|---|---|---|
| 1,532,463 A | | 4/1925 | Winterfiled |
| 1,539,299 A | | 5/1925 | Cheney |
| 3,718,132 A | | 2/1973 | Holt et al. |
| 3,851,651 A | | 12/1974 | Icenbice, Jr. |
| 4,180,079 A | | 12/1979 | Wing |
| 4,342,317 A | | 8/1982 | Axelgaard |
| 5,097,833 A | | 3/1992 | Campos |
| 5,336,255 A | * | 8/1994 | Kanare ........................ 607/149 |
| 5,350,415 A | | 9/1994 | Cywinski |
| 5,354,320 A | | 10/1994 | Schaldach et al. |
| 5,527,357 A | | 6/1996 | Springer, Jr. |
| 5,562,718 A | * | 10/1996 | Palermo ....................... 604/46 |
| 5,851,223 A | * | 12/1998 | Liss ............................. 607/46 |
| 5,947,897 A | * | 9/1999 | Otake .......................... 600/372 |

FOREIGN PATENT DOCUMENTS

| | | |
|---|---|---|
| CA | 1202683 | 4/1986 |
| CA | 2228817 | 8/1998 |
| EP | 0 057 561 A | 8/1982 |
| WO | WO 97 37720 A | 10/1997 |

* cited by examiner

Primary Examiner—George R. Evanisko
Assistant Examiner—Roderick Bradford

(57) ABSTRACT

An apparatus for providing therapeutic electrical signals has a plurality of sets of electrodes, each set of electrodes comprising at least two electrodes for applying the therapeutic electrical signal to a user. A switch selectively switches the therapeutic electrical signal to each of the electrodes in a predetermined pattern. The electrodes are arranged on a flexible platform which can substantially conform to surfaces of the user. The therapeutic electrical signal can be applied to the sets of electrodes in any predetermined pattern, including a predetermined pattern that sequentially sends the therapeutic electrical signal in a first direction to each set of electrodes. Preferably, the sets of electrodes comprise at least three electrodes arranged in a substantially chevron pattern with a center electrode having the opposite potential to the side electrode. The therapeutic electrical signal is generated by a signal generator. The signal generator generates different types of therapeutic electrical signals by applying a base wave with a frequency of about 150 KHz to 180 KHz at different frequencies between about 2 to 100 times in a second. The switch selectively switches the different types of therapeutic electrical signals in the predetermined pattern. The signal generator can decrease the therapeutic electrical signals from its maximum to its minimum within about 0.1 to 0.01 microseconds. The therapeutic electrical signal is switched to a next set of electrodes within about 0.5 to 2 seconds. The apparatus and method can be used in a variety of treatments, including relief of pain, relief of stress, electronic acupuncture and transcutaneous electrical nerve stimulation.

22 Claims, 6 Drawing Sheets

METHOD AND APPARATUS FOR ELECTROMEDICAL THERAPY

FIELD OF THE INVENTION

This invention relates to a method and apparatus for use in electromedical therapy. More particularly, the present invention relates to a method and apparatus for applying a therapeutic.electrical signal to regions of a user's body. The therapeutic signal could be used for any type of therapy, including to relieve pain, to relieve stress, to apply electronic acupuncture and for transcutaneous electrical nerve stimulation (TENS).

BACKGROUND OF THE INVENTION

In the past, several types of methods and apparatuses to apply an electrical signal in electromedical therapy have been used. However, the prior art methods and apparatuses generally provide a small number of electrodes to which the therapeutic electrical signal can be applied. This limits the area of the user's body to which the therapeutic signals can be applied at any one time. As a result, the duration of therapy and use of the apparatus by the user increase.

Furthermore, use of a small number of electrodes results in the electrical signal being applied to the same area for an extended period of time. This has been shown to create habituation effects. Habituation effects generally result from the body filtering out the therapeutic electrical signals being applied, thereby eliminating the positive effects of the therapeutic electrical signal. In addition, any benefit from the prior art device is usually limited to the time the therapeutic signals are applied, and does not provide any lingering effects.

Use of a small number of electrodes, such as in prior art devices, requires the prior art devices to be periodically moved over the user's body. In fact, some prior art devices have electrodes which can rotate to facilitate movement over the user's body. However, these prior art devices are generally difficult for users to use on themselves and require a therapist or assistant to apply the treatment. This is especially the case where the treatment is being applied to the user's back, and particularly the lower back, which is not easily accessible by the user.

Furthermore, the prior art devices by and large generate an electrical signal which could itself harm the user and/or cause pain. This results from the electrical signal having characteristics that damage the skin surface and otherwise hurt the patient or cause the patient discomfort. While the beneficial effects of the electrical signal often outweigh the temporary discomfort of the patient, this discomfort sometimes causes patients not to use the prior art electromedical apparatuses, or not use them as frequently as required in order to provide effective long-term therapy.

Accordingly, the prior art devices suffer from several disadvantages. One of these disadvantages include that the prior art devices generally only apply the electrical signal to a small region of the body at one time. Another disadvantage is that the prior art devices often require an assistant to apply the therapy. Another disadvantage is that the therapeutic effects of the prior art devices are limited by the corresponding habituative effects caused by the patient's own body. A further disadvantage is that the electrical signals applied by the prior art devices often cause pain, burns and/or other discomfort to the patient because of the nature and the shape of the electrical signal being applied. A still further disadvantage of the prior art devices is that their beneficial effects are limited to the duration of the procedure, and do not provide any lingering beneficial effects which continue after the procedure is completed.

SUMMARY OF THE INVENTION

Accordingly, it is an object of this invention to at least partially overcome the disadvantages of the prior art. Also, it is an object of this invention to provide an improved apparatus and method for providing therapeutic electrical signals.

Accordingly, in one of its objects, this invention resides in an apparatus for providing therapeutic electrical signals, said apparatus comprising: a signal generator for generating the therapeutic electrical signal; a plurality of sets of electrodes, each set of electrodes comprising at least two electrodes for applying the therapeutic electrical signal to a user; and a switching unit for selectively switching the therapeutic electrical signal to each set of electrodes in a predetermined pattern.

In a further aspect, the present invention resides in a method for providing therapeutic electrical signals, said method comprising the steps of: (a)generating a therapeutic electrical signal; (b) providing a plurality of sets of electrodes, each set of electrodes comprising at least two electrodes for applying the therapeutic electrical signal to a user; and (c) selectively switching the therapeutic electrical signal to each set of electrodes of the plurality of sets of electrodes in a predetermined pattern.

Accordingly, one advantage of the present invention is that a plurality of sets of electrodes are used to apply the therapeutic electrical signal. In this way, a large surface of the user can be treated at any one time without the need to move the apparatus over the user's body. This makes it easier to apply the therapeutic electrical signal to the user. Furthermore, this makes it easier for the user to use the apparatus on themselves without an assistant.

In a preferred embodiment, the electrodes are arranged on a platform which permits electrodes to substantially conform to the surface of the user. This facilitates application of the therapeutic electrical signal to regions of the user's body which are not generally flat. For example, this permits the platform to conform to variations in the user's back, such as around the spine. This facilitates application of the therapeutic electrical signal to the lower back of the patient, such as along the acupuncture meridian, which may result in release of enkefalins by the body to relieve stress.

A further advantage of the present invention is that it comprises a plurality of sets of electrodes to which the therapeutic electrical signal is applied in a predetermined pattern. Accordingly, while a large number of electrodes are available to be used in order to cover a large surface area of the user, the therapeutic electrical signal is only applied to a set of electrodes at any one time. In this way, the therapeutic electrical signal may be applied to electrodes proximate each other, permitting the therapeutic electrical signal to have a smaller electrical potential than would be required if the electrodes were distant from each other. Furthermore, this permits the switch to apply the therapeutic electrical signals in a predetermined pattern to achieve the best coverage and therapeutic benefit to the user. For example, in a preferred embodiment, the switch will apply the therapeutic electrical signal to a next set of electrodes in the plurality of electrodes every 0.5 to 2 seconds in order to avoid habituative effects.

A still further advantage of the present invention is that the therapeutic electrical signals can be applied to the sets of electrodes in a predetermined pattern. In this way, the user can control how the therapeutic electrical signals are applied, including the area, duration and type of therapeutic signal. Preferably, the predetermined pattern will be selected so as to decrease the habituation effect. The predetermined pattern can also be selected to provide lingering beneficial effects that continue after the procedure is completed. This can result, for example, by selecting a predetermined pattern that promotes generation of endorphins that are retained in the body. Furthermore, when the therapeutic electrical signal is applied to the acupuncture meridian, the body may generate enkefalins which will relieve stress. In addition, by applying the therapeutic electrical signal in a predetermined pattern as opposed to a random pattern, the user can be ensured that the therapeutic electrical signal will not be applied to the same set of electrodes consecutively. Applying the therapeutic electrical signal to the same set of electrodes consecutively could result in overexposure of the therapeutic electrical signals to a particular region of the user's body that may cause discomfort to the patient and/or promote habituation effects.

A further advantage of the present invention is that the therapeutic electrical signal can have characteristics which may decrease or eliminate pain while maintaining an effective therapeutic level. This is accomplished, in part, by the therapeutic electrical signal comprising a base wave having a relatively high frequency of about 150 KHz to 180 KHz and more preferably 160 to 170 KHz. The base wave is preferably applied about 2 to 100 times per second. In order to decrease pain that may be associated with the therapeutic electrical signals, the base wave of the therapeutic electrical signal preferably decreases from its maximum to its minimum in about 0.2 to 0.01 microseconds. In a further preferred embodiment, the integral of the base wave over a cycle is zero.

A still further advantage of the present invention is that the predetermined pattern may comprise different types of therapeutic electrical signals. In other words, the switching unit will selectively switch between different types of therapeutic electrical signals to each set of electrodes in a predetermined pattern. In this way, the patient will be exposed to different types of therapeutic electrical signals that may have different beneficial effects. In addition, by changing the types of therapeutic electrical signals being applied, the habituation effects may also decrease. In this way, changing the types of therapeutic electrical signals, as well as limiting the duration that the switch may apply the therapeutic electrical signal to each set of electrodes to about 0.5 to 2 seconds, reduces the effects of the brain filters thereby reducing habituation effects, and may cause lingering beneficial effects which continue after the therapy is completed.

Further aspects of the invention will become apparent upon reading the following detailed description and drawings which illustrate the invention and preferred embodiments of the invention.

BRIEF DESCRIPTION OF THE DRAWINGS

In the drawings, which illustrate embodiments of the invention.

DETAILED DESCRIPTION OF THE PREFERRED EMBODIMENTS

Figure 1A:
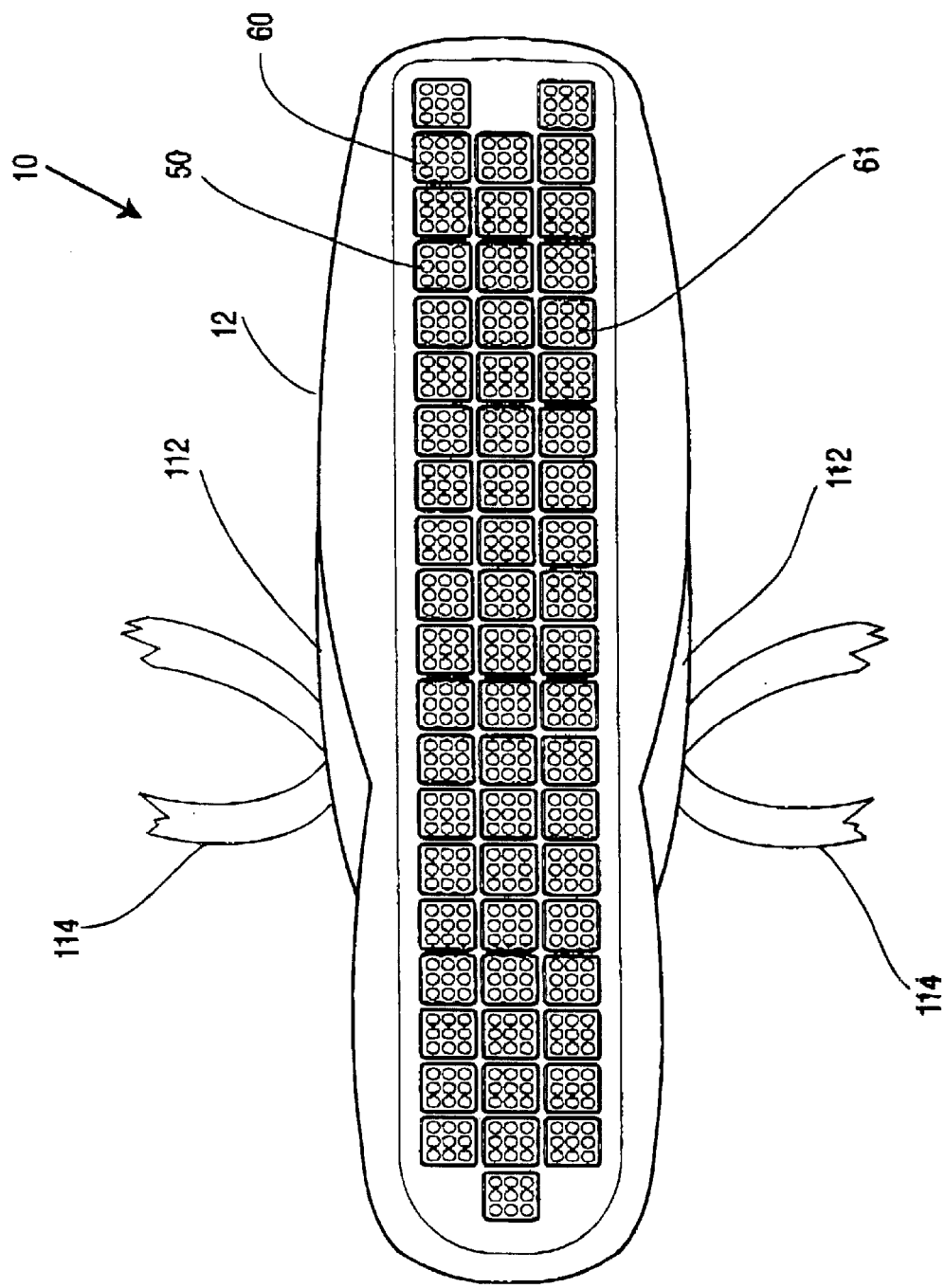
FIGS. 1A and 1B are bottom and side views, respectively, of a device according to one embodiment of the present invention.
Figure 1B:
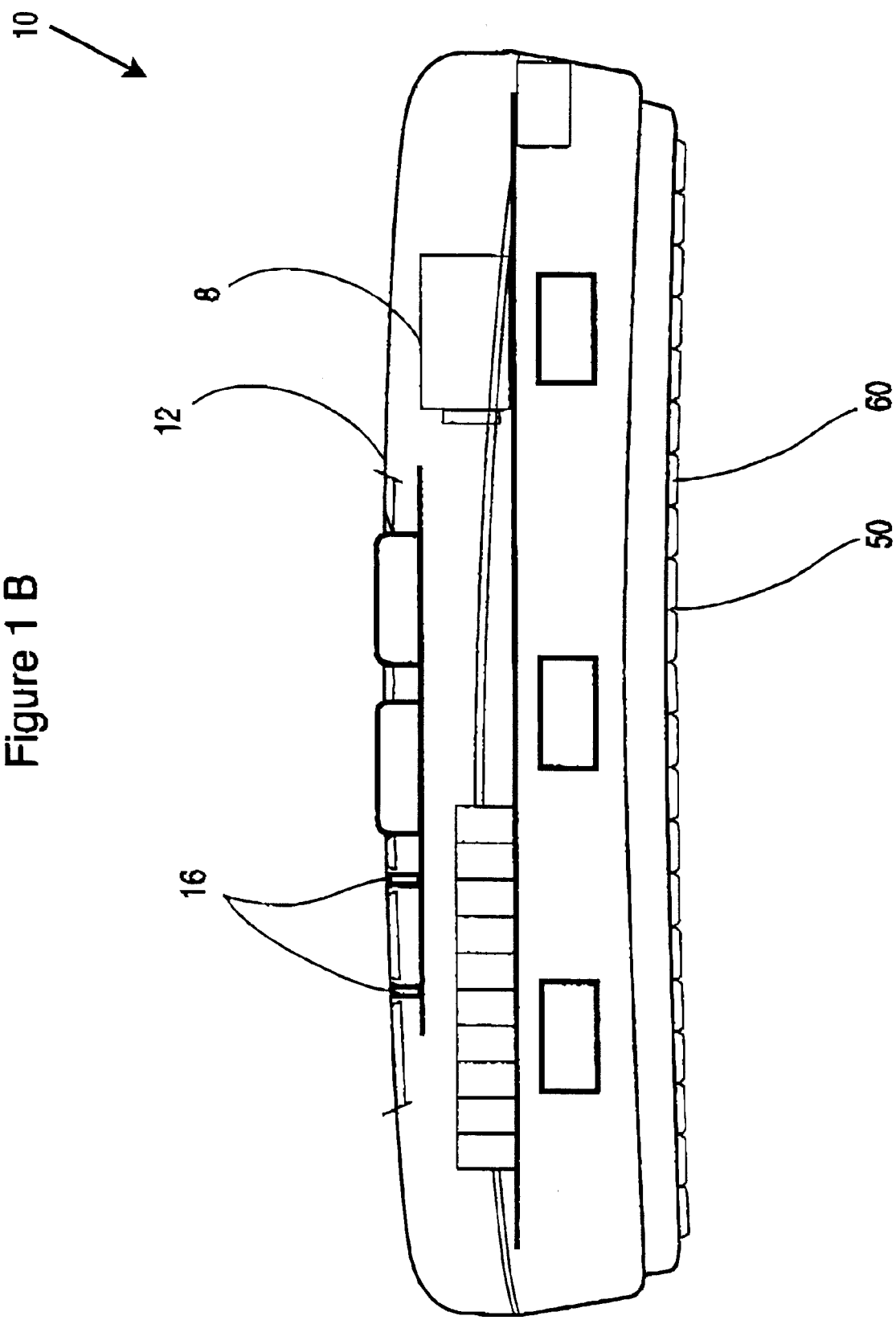

FIG. 1A is a bottom elevation view and FIG. 1B is a side elevation view of an apparatus, shown generally by reference numeral 10, for providing therapeutic electrical signals according to one embodiment of the present invention. As shown in FIGS. 1A and 1B, the apparatus 10 comprises a housing 12 which houses the plurality of electrodes 60. The housing 12 also houses other components, including input/output devices, such as a keypad and LEDs 16, as well as a power source, such as battery pack 8. The housing 12 preferably has an opening for straps 114. In this way, the apparatus 10 can be strapped or fastened to a part of the user, such as the lower back or a leg, with straps 114.

In a preferred embodiment, the plurality of electrodes 60 are mounted on a platform 50 that permits relative movement of the electrodes 60. In this way, the platform 50 and/or the plurality of electrodes 60 on the platform 50 will be able to substantially conform to a surface of the user so that each of the plurality of electrodes 60 is in contact with a surface of the user, even if the surface of the user is not a flat surface. For example, the platform 50 may be flexible to permit the electrodes to substantially conform to the surface of the body. In one preferred embodiment, the platform 50 is made from a flexible, non-conductive material, such as rubber, which permits the plurality of electrodes 60 to substantially conform to a surface of the user and also electrically insulates the plurality of electrodes 60 from each other. In the alternative, the plurality of electrodes 60 could move relative to the platform 50, but be biased outwards so as to substantially conform to the surface of the patient. In either case, it is apparent that the platform 50 would permit the plurality of electrodes 60 to substantially conform to a surface of the user.

As also shown in FIG. 1A, the plurality of electrodes 60 preferably comprise nipples 61. The plurality of electrodes 60 may comprise at least one, and preferably more, nipples 61 to assist in decreasing the electrical contact resistance between the plurality of electrodes 60 and the surface of the user. In the preferred embodiment, shown in FIG. 1A, each electrode 60 has nine nipples 61.

Figure 2:
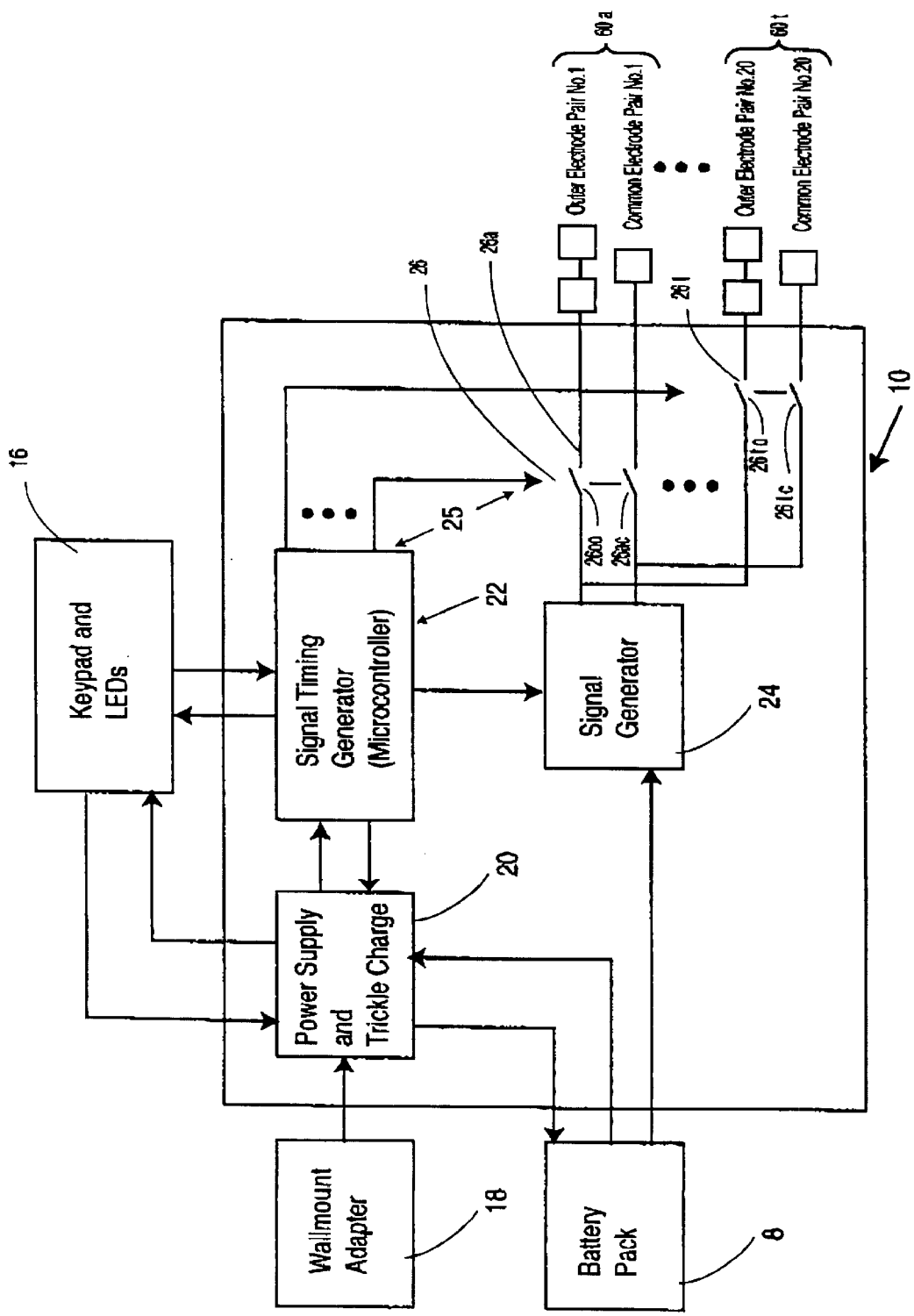
FIG. 2 is a schematic diagram showing the components of the apparatus for applying the therapeutic electrical signal.

FIG. 2 is a schematic diagram symbolically showing the components of the apparatus 10 for applying the therapeutic electrical signal according to one embodiment. As shown in FIG. 2, the apparatus 10 comprises input/output devices, such as a keypad and LEDs 16, as well as a power source, such as a battery pack 8, which are also illustrated in FIGS. 1A and 1B. As illustrated in FIG. 2, the apparatus 10 can also comprise a wall mount adapter 18 and a power supply and trickle charger 20, which together form a power unit to both supply power to the apparatus 10 and charge the battery pack 8 for later use.

The power supply and trickle charger 20 is connected to the keypad and LED 16 to supply power to this component.

The keypad and LED 16, together with the power supply and trickle charger 20, are connected to the signal timing generator 22 to both supply power to the signal timing generator 22 and also send and receive input/output signals from the keypad and LED 16. Preferably, the keypad and LED 16 can send and receive input/output signals to the signal timing generator 22 which specify predetermined patterns and types of therapeutic electrical signals which should be applied to the plurality of electrodes 60 and which predetermined patterns are being applied.

In a preferred embodiment, the signal timing generator 22 comprises a microcontroller, such as a microprocessor. The signal timing generator 22 is connected to a plurality of switches 26. The signal timing generator 22 actuates the plurality of switches 26 to selectively switch the therapeutic electrical signal to the plurality of electrodes 60. The plurality of electrodes 60 are grouped into a plurality of sets of electrodes 60a to 60t. The switches 26 selectively switch the therapeutic electrical signal to each of the sets of electrodes 60a to 60t in a predetermined pattern.

As shown in FIG. 2, the first group of switches 26a switch the therapeutic electrical signal to the first set 60a of the plurality of sets of electrodes 60a to 60t. The first set of electrodes 60a, in this embodiment, comprises the outer electrode pair no. 1 and the common electrode no. 1. Accordingly, in this embodiment, the first set of electrodes 60a comprises three electrodes, namely a common electrode in the centre and a pair of outer electrodes. As also shown in FIG. 2, the apparatus 10 comprises a 20th set of electrodes 60t comprising outer electrode pair no. 20 and common electrode no. 20. Therefore, the 20th set of electrodes 60t also comprises three electrodes with a common electrode in the centre and a pair of outer electrodes. The signal timing generator 22 switches the therapeutic electrical signal to the 20th set of electrodes 60t by actuating the 20th group of switches 26t. While not shown in FIG. 2, it is apparent that the plurality of switches 26 would comprise switches 26b to 26s to switch the therapeutic electrical signal to each set of electrodes 60b to 60s.

In the embodiment shown in FIG. 2, there are 20 sets of electrodes comprising three electrodes for a total of 60 electrodes. However, it is understood that different sets of electrodes and different numbers of electrodes in each set can be used.

Together, the signal timing generator 22 and the plurality of switches 26 form the switching unit, shown generally by reference numeral 25. The switching unit 25 is used to send the therapeutic electrical signals selectively to each of the plurality of sets of electrodes 60a to 60t in a predetermined pattern.

The therapeutic electrical signal is generated by the signal generator 24. The signal generator 24 will generate a base signal or base wave $b_w$ that is then selectively switched by the switching unit 25 to each one of the plurality of sets of electrodes 60a to 60t. The signal generator 24 is connected to the signal timing generator 22 to control the base wave $b_w$ so as to produce the predetermined pattern and control the type of therapeutic electrical signal being generated. The signal generator 24 is also connected to a power source, which in this embodiment is the battery pack 8, to draw sufficient power to generate the therapeutic electrical signal and the base wave $b_w$ that forms the therapeutic electrical signal.

Figure 4:
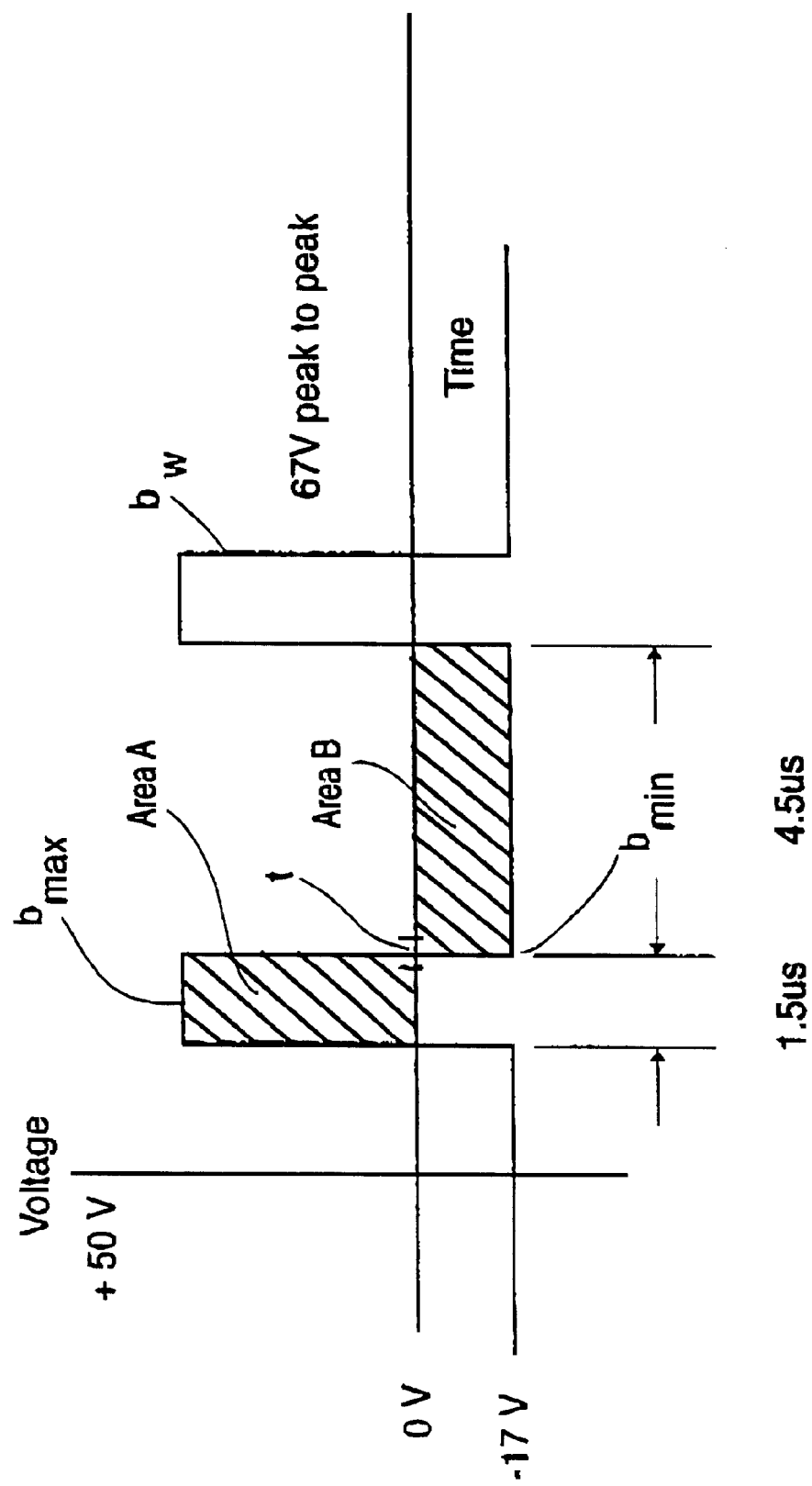
FIG. 4 is a timing diagram showing the base wave according to one embodiment of the present invention.

In a preferred embodiment, the base wave $b_w$ will have a wave form shown in FIG. 4 by reference numeral $b_w$. In a preferred embodiment, the base wave $b_w$ will have a frequency of between 150 KHz to 180 KHz, and more preferably 160 KHz to 170 KHz. In the preferred embodiment shown in FIG. 4, the base wave $b_w$ has a frequency of about 166 KHz.

At a frequency of 166 KHz, the period of the base wave $b_w$ will be about 6 microseconds. Preferably, the base wave $b_w$ will decrease quickly from its maximum to its minimum. For example, as shown in FIG. 4, the base wave $b_w$ will decrease from its maximum value $b_{max}$ of about positive 50V to its minimum value $b_{min}$ of about negative 17V in a time t which preferably is within about 0.2 to 0.01 microseconds and still more preferably within about 0.1 to 0.01 microseconds. In a preferred embodiment, the time t is most preferable about 0.05 microseconds. By having the base wave $b_w$ decrease from the maximum $b_{max}$ to its minimum $b_{min}$ within this relatively short time period, it has been found that the pain, burns, and other discomfort felt by the patient is greatly decreased.

From analysis of the base wave $b_w$ shown in FIG. 4, it is also apparent that the integral of the base wave $b_w$ over time will be zero. This is apparent from FIG. 4 which illustrates that the Area A between $b_{max}$ and zero is approximately equal to the Area B between $b_{min}$ and zero. This is the case because the value $b_{max}$ is about positive 50V and lasts for a duration of 1.5 microseconds while the voltage $b_{min}$ is about a third of that, namely negative 17V, but lasts for three times as long, namely about 4.5 microseconds. Accordingly, Area A is substantially equal to Area B, which illustrates that the integral of the base wave $b_w$ over time will be zero. This also illustrates that the net charge imposed on the user by each electrode over a period of the base wave $b_w$ will always be zero. As the therapeutic electrical signal comprises the base wave $b_w$, the integral over time of the therapeutic electrical signal will also be zero. It has been found that by having a base wave $b_w$, and therefore a therapeutic electrical signal, with an integral over time of about zero, the overall pain, burns and discomfort suffered by the patient greatly decreases.

As stated above, the therapeutic electrical signal comprises the base wave $b_w$. However, it is preferred that the therapeutic electrical signal is not identical to the base wave $b_w$. Rather, it is preferred that the therapeutic electrical signal comprises bursts of the base wave $b_w$. In other words, the therapeutic electrical signal preferably comprises bursts of the base wave $b_w$ at specific frequencies, such as 2 to 100 times in a second, and the base wave $b_w$ would be quiet or not applied at other times.

Figure 5A:
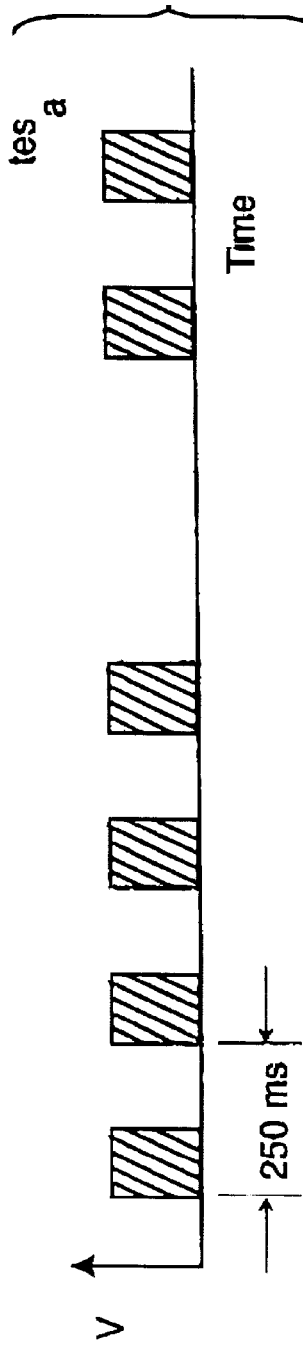
FIGS. 5A, 5B and 5C are timing diagrams showing different types of therapeutic electrical signals that may be applied in a predetermined pattern according to one embodiment of the present invention.

FIG. 5A shows a first therapeutic electrical signal $tes_a$ where the base wave $b_w$ is applied four times in a second. Therefore, the first therapeutic electrical signal $tes_a$ has a period of about 250 milliseconds and a frequency of 4 Hz. During the period of 250 milliseconds, the base wave $b_w$ is applied for about half that time, or 125 milliseconds. For the remaining period, namely 125 milliseconds, the base wave $b_w$ is not applied.

Figure 5B:
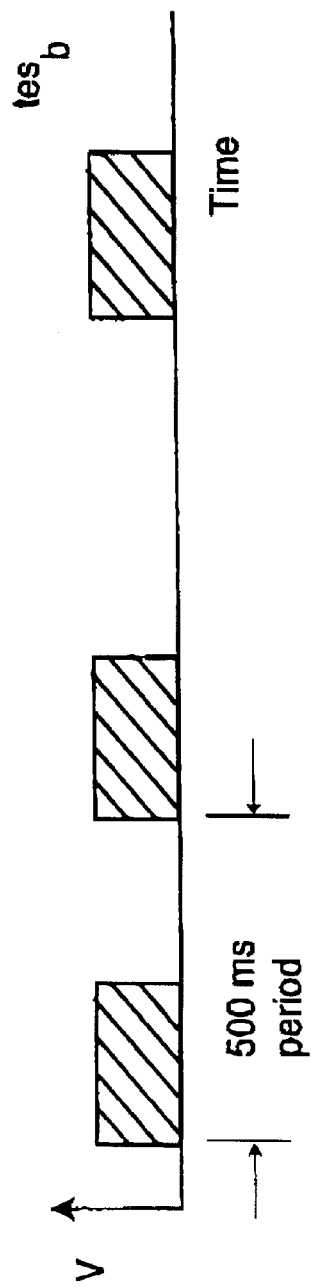

FIG. 5B shows a second therapeutic electrical signal $tes_b$ where the base wave $b_w$ is applied two times in a second. The second therapeutic electrical signal $tes_b$ is applied in a burst of about 250 milliseconds and then is quiet or not applied for about 250 milliseconds. Accordingly, the second therapeutic electrical signal $tes_b$ has a period of about 500 milliseconds and a frequency of about 2 Hz.

Figure 5C:
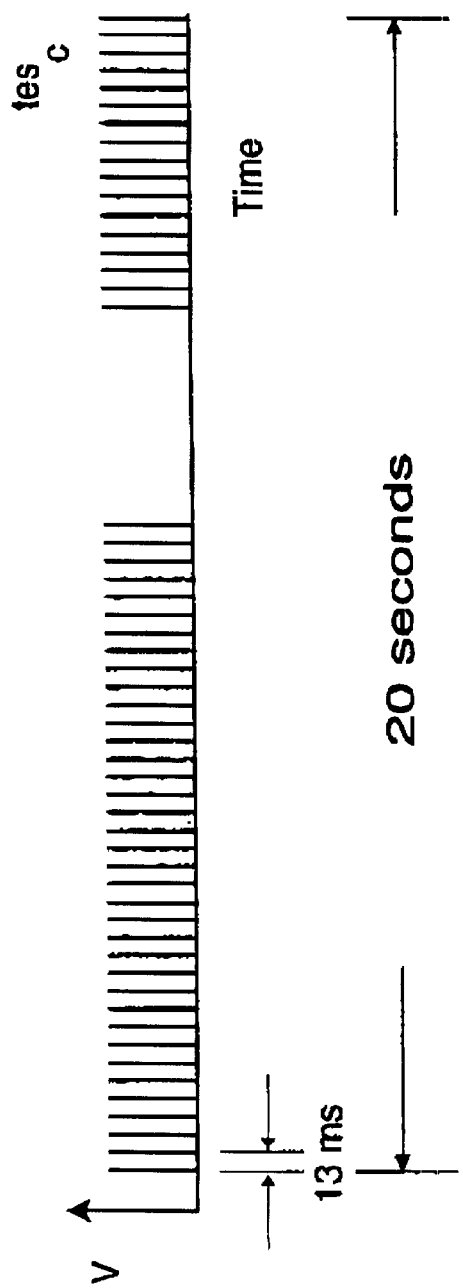

FIG. 5C shows a third therapeutic electrical signal $tes_c$ that has a period of about 13 milliseconds, and therefore a frequency of about 77 Hz. In this embodiment, the base wave $b_w$ is applied for a burst of about 3 milliseconds followed by a quiet period where the base wave $b_w$ is not applied for about 10 milliseconds. In this way, the third electrical signal $tes_c$ applies the base wave $b_w$ 77 times in a second, but for only about 3 milliseconds each time.

The apparatus 10 can apply any of the therapeutic electrical signal $tes_a$, $tes_b$, $tes_c$, or any other type of therapeutic electrical signal. In a preferred embodiment, the therapeutic electrical signal will comprise a base wave $b_w$ applied at a frequency of about 2 to 100 times per second. As shown in FIGS. 5A, 5B and 5C, the duration or burst during which the base wave $b_w$ is applied can vary and may not correspond to half of the period, as illustrated by the third therapeutic electrical signal $tes_c$ in FIG. 5C. Furthermore, the predetermined pattern of the apparatus 10 may comprise different types of therapeutic electrical signals, as described more fully below.

Figure 3:
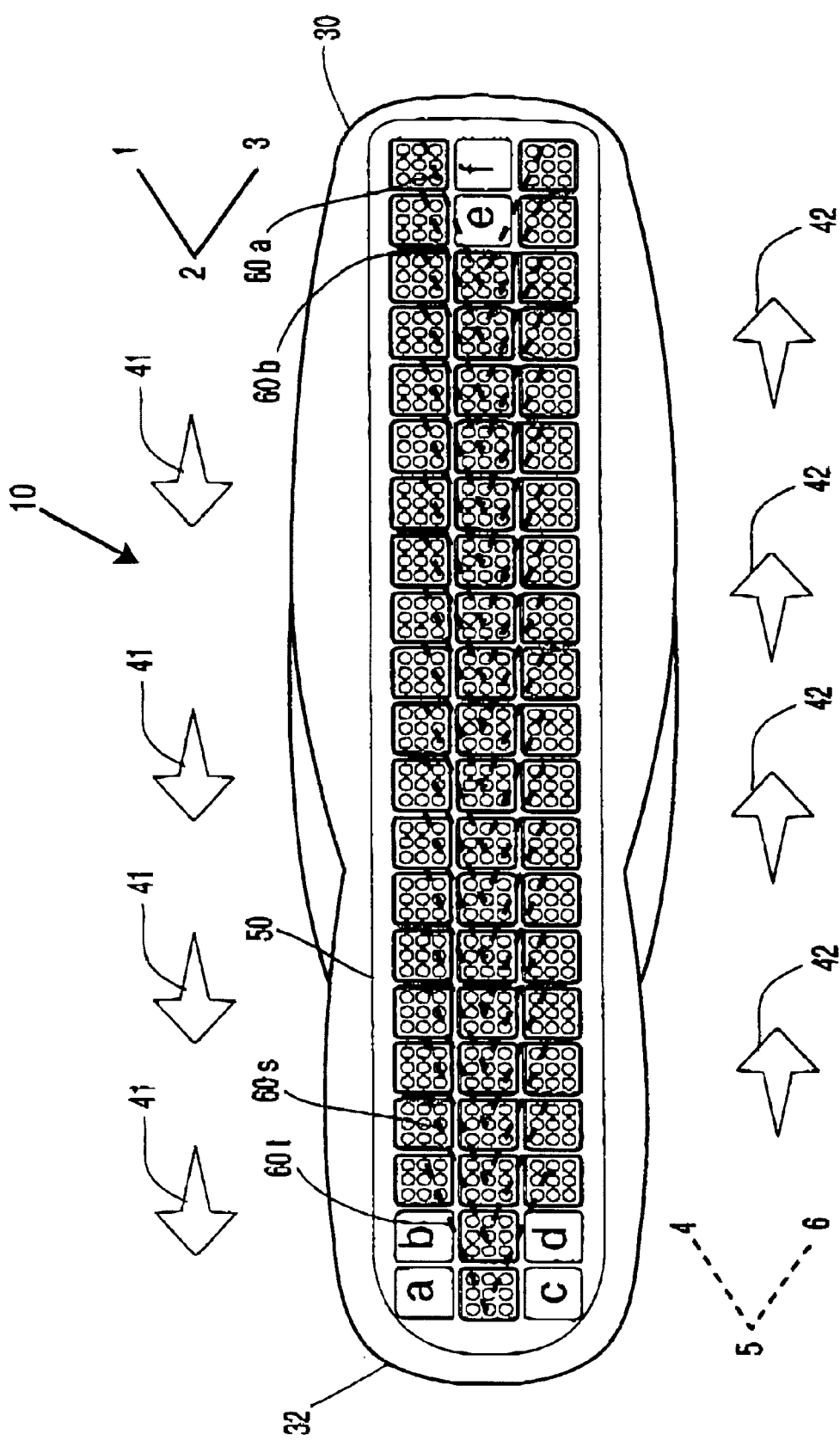
FIG. 3 is a bottom elevation view of the device according to one embodiment of the present invention.

FIG. 3 shows the bottom elevation of the apparatus 10, similar to the view shown in FIG. 1A. In a preferred embodiment as illustrated in FIG. 3, each of the plurality of sets of electrodes 60a to 60t comprise at least three electrodes 60 arranged in a substantially chevron pattern. For example, the first set of electrodes 60a shown in FIG. 3 comprise electrodes 1, 2 and 3. Likewise, the last set of electrodes 60t comprise electrodes 4, 5 and 6. It is apparent that the twenty chevron patterns between the first set of electrodes 60a and the last set of electrodes 60t illustrate each set of the plurality of sets of electrodes 60a to 60t of the embodiment illustrated in FIG. 3.

It is preferable that the centre electrode, such as electrodes 2 and 5, of the plurality of sets of electrodes 60a to 60t, have a potential that is opposite to the potential of the side electrodes 1, 3 and 4, 6. To accomplish this, centre electrodes 2, 5 may have different electrical switches 26 from the side electrodes. This is illustrated in FIG. 2 where the first group of switches 26a comprise switches 26ao and 26ac. Switch 26ao actuates the outer electrode pair no. 1 corresponding to electrodes 1 and 3 and switch 26ac actuates the common electrode no. 1 corresponding to electrode 2. Likewise, the 20th group of switches 26 comprise switches 26tc and 26to. Switch 26th actuates the outer electrode pair no. 20 corresponding to electrodes 4 and 6 and switch 26tc actuates the common electrode no. 20 corresponding to electrode 5.

It is understood that the chevron pattern of electrodes illustrated in FIG. 3 is a preferred embodiment and is selected to permit a relatively large area to be effected by the therapeutic electrical signal, while at the same time having the electrodes fairly near each other so that the voltage may not be too large to overcome the natural resistance of the body. Nevertheless, it is understood that other arrangements of electrodes, other than a chevron pattern, including a square pattern, a circular or semi-circular pattern or even a straight line, could be used provided each set of electrodes 60a to 60t have at least two electrodes through which the therapeutic electrical signal may pass.

In the embodiment shown in FIG. 3 where a chevron pattern is used, it is apparent that not all of the plurality of electrodes 60 will have an electrical signal passing through them. For example, electrodes a, b, c, d, e, f do not form a chevron pattern with other electrodes, and therefore would not be used in the embodiment shown in FIG. 3. However, if another pattern, such as a straight line is used, then electrodes a, b, c, d, e, f may have electrical signal passing through them.

As stated above, the switching unit 25 will apply the therapeutic electrical signal to the plurality of sets of electrodes 60a to 60t in the predetermined pattern. The predetermined pattern may be any pattern that switches the therapeutic electrical signal to each set of electrodes 60a to 60t in a controlled manner without causing the therapeutic electrical signal to be switched to the same set of electrodes twice, thereby causing habituation effects.

In a preferred embodiment, the switching unit 25 will send the therapeutic electrical signal sequentially to each set of electrodes 60a to 60t. For example, as shown in FIG. 3, the switching unit 25 will send the therapeutic electrical signal sequentially in a consecutive order commencing with the first set of electrodes 60a at a first end 30 of the apparatus 10 and ending at the last set of electrodes 60t at the second end 32 of the apparatus 10. The switching unit 25 may have a predetermined pattern which continuously and repeatedly sends the therapeutic electrical signal sequentially in this consecutive order from the first set of electrodes 60a to the last set of electrodes 60t. Alternatively, the switching unit 25 may have a predetermined pattern which sends the therapeutic electrical signal in alternate directions "sweeping" across the platform 50.

For example, as shown in FIG. 3, the switching unit 25 may first apply the therapeutic electrical signals in a first direction, shown generally by the arrows marked with reference numeral 41, from the first end 30 to the second end 32. The switching unit 25 may then apply the therapeutic electrical signal in a second direction, shown generally by the arrows marked with reference numeral 42, from the second end 32 to the first end 30. For present purposes, a sweep is considered to be an application of therapeutic electrical signals once across each of the sets of electrodes 60a to 60t in either direction 41, 42 "sweeping" across the platform 50.

In the embodiment illustrated in FIG. 3, the sets of electrodes 60a to 60t in the first direction 41 will be the same as the sets of electrodes 60t to 60a in the second direction 42. In other words, the therapeutic electrical signal will be applied to the same three electrodes in each set of electrodes 60a to 60t in both directions 41, 42. However, the present invention is not limited to this embodiment. Rather, the sets of electrodes 60a to 60t in the first direction 41 may differ from the sets of electrodes 60a to 60t in the second direction 42, provided there are at least two electrodes 60 in each set of electrodes 60a to 60t.

In addition, the therapeutic electrical signal need not be the same in each direction. Rather, in a preferred embodiment, the therapeutic electrical signal will change with each "sweep". For example, as set out in Table A below, in sweep 1, which preferably is in a first direction 41, the therapeutic electrical signal will correspond to the first therapeutic electrical signal $tes_a$ shown in FIG. 5A and will be sequentially and consecutively applied to each of the plurality of sets of electrodes 60a to 60t. In sweep 2, which is preferably in the second direction 42, the therapeutic electrical signal will correspond to the second therapeutic electrical signal $tes_b$ illustrated in FIG. 5B. Likewise, in sweep 3, which is preferably in the first direction 41, the therapeutic electrical signal will correspond to the third therapeutic electrical signal $tes_c$ illustrated in FIG. 5C.

TABLE A

| Sweep | Quiet (ms) | Burst (ms) | Period (ms) | Bursts per sets of electrodes | Bursts per sweep (20 sets of electrodes 60) | Duration of sweep (sec) | Duration for each set of electrodes (sec) |
| --- | --- | --- | --- | --- | --- | --- | --- |
| 1 | 125 | 125 | 250 | 4 | 80 | 20 | 1 |
| 2 | 250 | 250 | 500 | 2 | 40 | 20 | 1 |
| 3 | 10 | 3 | 13 | 77 | 154 | 20.02 | 1 |

One advantage of the above is that the application of the base wave $b_w$ at the different frequencies, namely 4 Hz, 2 Hz and 77 Hz, will have different beneficial effects to the patient. For example, a frequency of about 77 Hz has been found to generate endorphins, and enkefalins which tend to relieve stress, and therefore it is preferred for a pain killing effect. Generation of enkefalins have been found to be most pronounced when the apparatus 10 is applied to the acupuncture meridians along the lower back region. The frequencies of 2 Hz and 4 Hz have been found to generate endorphins.

Accordingly, the apparatus 10 can apply the therapeutic electrical signals to the sets of electrodes 60a to 60t in a predetermined pattern. In addition, the predetermined pattern of the apparatus 10 can comprise different types of therapeutic electrical signals $tes_a$, $tes_b$, $tes_c$ at different stages.

It has been found that, preferably, the therapeutic electrical signal is applied to a set of electrodes 60a to 60t for about 0.5 to 2 seconds. For example, as illustrated in Table A above, the therapeutic electrical signals are applied to each set of electrodes 60a to 60t for a duration of about 1 second. In this way, as there are about 20 sets of electrodes in the embodiment shown in FIG. 3, each sweep from one end 30 or 32 to the other end 32 or 30 will take about 20 seconds. The predetermined pattern shown in Table A which comprises three sweeps and three types of therapeutic electrical signals $tes_a$, $tes_b$, $tes_c$ will therefore take about one minute. Preferably, the switch to a next set of electrodes 60a to 60t will occur during a quiet period when the base wave $b_w$ is not being applied.

The duration of 0.5 to 2 seconds is preferable because it is sufficient to generate endorphins and enkefalins. However, in addition, a duration of 0.5 to 2 seconds is generally insufficient to permit the body to generate hormones that counteract the beneficial effects of endorphins and enkefalins. Accordingly, by having in a predetermined pattern where the switching unit 25 switches the therapeutic electrical signal to a next set of electrodes within 0.5 to 2 seconds, habituation effects may decrease and the user may experience a build-up of endorphins and enkefalins. In this way, the user may experience a lingering effect from use of the apparatus 10, at least in part because of the build-up of endorphins and enkefalins caused by the use of the apparatus 10.

Likewise, it has been found that by having a redetermined pattern that comprises different types of herapeutic electrical signals $tes_a$, $tes_b$, $tes_c$, habituation effects may be further decreased because use of different types of therapeutic electrical signals $tes_a$, $tes_b$, $tes_c$ may bypass the brain filters which cause the habituation effects. Habituation effects have been found to be further decreased by applying the different types of therapeutic electrical signals $tes_a$, $tes_b$, $tes_c$ to the user for a duration of not more than 0.5 to 2 seconds per set of electrodes 60a to 60t. Moreover, applying different types of therapeutic electrical signals $tes_a$, $tes_b$, $tes_c$ will also produce different types of beneficial effects, such as generation of endorphins, as well as generation of enkefalins. Accordingly, generating and applying different types of therapeutic electrical signals, $tes_a$, $tes_b$, $tes_c$ across a plurality of electrodes 60 not only helps to decrease habituation effects, but also provides more than one type of benefit to the user, and, the benefit the user may experience is more likely to linger after use of the apparatus 10 has ceased.

It is clear that the therapeutic electrical signals will have any type of voltage or current required to produce a therapeutic effect as persons skilled in the art may select. More particularly, while the present invention has been described with respect to therapeutic electrical signals having a base wave $b_w$ of a particular voltage, it is understood that the present invention is not limited to therapeutic electrical signals having this particular voltage, but rather would include any voltage that would produce therapeutic effects. In addition, the present invention may be used for different types of therapies, including relief of pain, relief of stress, electronic acupuncture and transcutaneous electrical nerve stimulation (TENS), and, the precise voltage and current of the base wave $b_w$ of the therapeutic electrical signals for each of these therapies may differ. Preferably, an electro conductive cream, as is known in the art, should preferably be applied to the surface of the user to improve the electrical contact between the plurality of electrodes 60 and the user, thereby decreasing contact resistance.

In addition, while the present invention has been described with respect to three types of therapeutic electrical signals, $tes_a$, $tes_b$, $tes_c$, it is understood that the invention is not restricted to these particular three types of therapeutic electrical signals. While these three types of therapeutic electrical signals $tes_a$, $tes_b$, $tes_c$ have been found to be preferred therapeutic electrical signals, other types of therapeutic electrical signals may also be used in the predetermined pattern of this invention.

It will be understood that, although various features of the invention have been described with respect to one or another of the embodiments of the invention, the various features and embodiments of the invention may be combined or used in conjunction with other features and embodiments of the invention as described and illustrated herein.

Although this disclosure has described and illustrated certain preferred embodiments of the invention, it is to be understood that the invention is not restricted to these particular embodiments. Rather, the invention includes all embodiments which are functional, mechanical or electrical equivalents of the specific embodiments and features that have been described and illustrated herein.

The embodiments of the invention in which an exclusive property or privilege is claimed are defined as follows:

1. An apparatus for providing therapeutic electrical signals, said apparatus comprising:

a signal generator for generating the therapeutic electrical signal comprising a base wave having a frequency between 150 KHz to 180 KHz, said base wave being applied at a frequency of between about 2 to 100 times in a second;

a plurality of sets of electrodes, each set of electrodes comprising at least two electrodes for applying the therapeutic electrical signal to a user; and a switching unit for selectively switching the therapeutic electrical signal from one set of electrodes of the plurality to another set of electrodes of the plurality in a predetermined pattern at intervals of between 0.5 to 2 seconds;

wherein the base wave of the therapeutic electric signal decreases from a maximum voltage to a minimum voltage within about 0.2 to 0.01 microseconds.

2. The apparatus as defined in claim 1 further comprising:
a platform upon which the plurality of sets of electrodes is arranged; and wherein the platform permits the electrodes to substantially conform to a surface of the user, such that each of the electrodes of the plurality of sets of electrodes is adapted to be in electrical contact with the surface of the user.

3. The apparatus as defined in claim 2 wherein the predetermined pattern comprises the switching unit switching the therapeutic electrical signal consecutively to each set of electrodes commencing with a first set of electrodes near a first end of the apparatus and ending at a last set of electrodes near a second end of the apparatus; and wherein the switching unit selectively switches the therapeutic electrical signal to each set of electrodes in intervals of between 0.5 to 2 seconds.

4. The apparatus as defined in claim 1 wherein the predetermined pattern comprises the switching unit sequentially switching the therapeutic electrical signal in a first direction consecutively to each set of electrodes.

5. The apparatus as defined in claim 1 wherein the predetermined pattern comprises the switching unit switching the electrical therapeutic signal consecutively in a first direction from a first end of the apparatus to a second end of the apparatus and then consecutively in a second direction from the second end to the first end.

6. The apparatus as defined in claim 5 wherein the sets of electrodes in the first direction correspond to the sets of electrodes in the second direction.

7. The apparatus as defined in claim 1 wherein each set of electrodes comprise at least three electrodes arranged in a substantially chevron pattern with at least a centre electrode and at least two side electrodes; and wherein the centre electrode has a potential opposite to the side electrodes when the therapeutic electrical signal is applied.

8. The apparatus as defined in claim 1 wherein the signal generator generates a first type of therapeutic electrical signal comprising the base wave applied at a first frequency between 2 to 100 times in a second and a second type of therapeutic electrical signal comprising the base wave applied at a second frequency of about 2 to 100 times in a second wherein the first frequency differs from the second frequency;

wherein the switching unit selectively switches the first type and the second type of therapeutic electrical signal to each set of electrodes in the predetermined pattern.

9. The apparatus as defined in claim 8 wherein an integral against time of the base wave of the therapeutic electric signals over a period of the base wave is substantially zero.

10. The apparatus as defined in claim 9 wherein the maximum voltage of the base wave is about positive 50V and the minimum voltage of the base wave is about negative 17V, wherein over the period of the base wave the minimum voltage will be applied about three times as long as the maximum voltage such that the integral against time of the base wave over the period is substantially zero.

11. The apparatus as defined in claim 1 wherein the signal generator generates a first type of therapeutic electrical signal comprising the base wave applied at a frequency of about 77 Hz such that the base wave is applied for a burst of about 3 milliseconds followed by a quiet period where the base wave is not applied for about 10 milliseconds.

12. A method for providing therapeutic electrical signals, said method comprising the steps of:

a) generating a therapeutic electrical signal comprising a base wave having a frequency between 150 KHz to 180 KHz, said base wave being applied at a frequency of between about 2 to 100 times in a second;

b) providing a plurality of sets of electrodes, each set of electrodes comprising at least two electrodes for applying the therapeutic electrical signal to a user; and c) selectively switching the therapeutic electrical signal to each set of electrodes of the plurality of sets of electrodes in a predetermined pattern in intervals of between 0.5 and 2 seconds;

wherein the base wave of the therapeutic electrical signal decreases from a maximum voltage to a minimum voltage within about 0.2 to 0.01 microseconds.

13. The method as defined in claim 12 further comprising the step of:

b1) providing the plurality of sets of electrodes on a platform that permits electrodes to substantially conform to a surface of the user so that substantially all of the electrodes of the plurality of electrodes is in electrical contact with the surface of the user.

14. The method as defined in claim 13 further comprising the step of:

c1) selectively switching the therapeutic electrical signal to each set of electrodes consecutively commencing with a first set of said plurality of sets of electrodes near a first end of the platform and ending at a last set of said plurality of sets of electrodes at a second end of the platform.

15. The method as defined in claim 14 wherein an integral against time of the base wave of the therapeutic electric signal over a period of the base wave is substantially zero.

16. The method as defined in claim 12 further comprising the step of:

b3) providing each set of electrodes with at least three electrodes arranged in a substantially chevron pattern having a center electrode and at least two side electrodes.

17. The method as defined in claim 12 wherein the base wave of the therapeutic electrical signal decreases from a maximum voltage to a minimum voltage within about 0.1 to 0.01 microseconds.

18. The method as defined in claim 12 further comprising the steps of:

a1) generating a first type of therapeutic electrical signal by applying the base wave at a first frequency between 2 to 100 times in a second;

a2) generating a second type of therapeutic electrical signal by applying the base wave at a second frequency between 2 to 100 times in a second, wherein the first frequency is different from the second frequency; and c1) selectively switching the first type and the second type of therapeutic electrical signals to each set of electrodes in the predetermined pattern.

19. The method as defined in claim 12 further comprising:

c1) selectively switching the therapeutic electrical signal to each set of electrodes in the predetermined pattern by switching the therapeutic electrical signal consecutively in a first direction from a first end of the apparatus to a second end of the apparatus and then consecutively in a second direction from the second end to the first end.

20. The method as defined in claim 19 further comprising:

a1) generating a first type of therapeutic electrical signal by applying the base wave applied at a first frequency between 2 to 100 times in a second:

a2) generating a second type of therapeutic electrical signal by applying the base wave at a second frequency between 2 to 100 times in a second, wherein the first frequency is different from the second frequency; and c2) selectively switching the first type and the second type of therapeutic electrical signal to each set of electrodes in the predetermined pattern by switching the first type of the therapeutic electrical signal consecutively in the first direction and then consecutively in the second direction, and, then switching the second type of therapeutic electrical signal consecutively in the first direction and then consecutively in the second direction.

21. The method as defined in claim 12 further comprising the step of generating a first type of therapeutic electrical signal by applying the base wave at a frequency of 77 Hz such that the base wave is applied for a burst of about 3 milliseconds followed by a quiet period where the base wave is not applied for about 10 milliseconds.

22. An apparatus for providing therapeutic electrical signals, said apparatus comprising:

signal generation means for generating the therapeutic electrical signal comprising a base wave having a frequency between 150 KHz to 180 KHz, said base wave being applied at a frequency of between about 2 to 100 times in a second;

a plurality of sets of electrodes, each set of electrodes comprising at least two electrodes for applying the therapeutic electrical signal to a user;

switching means for selectively switching the therapeutic electrical signal from one set of electrodes of the plurality to another set of electrodes of the plurality in a predetermined pattern at intervals of between 0.5 to 2 seconds;

wherein the signal generating means generates the base wave of the therapeutic electrical signal such that the base wave has a positive voltage portion having a maximum voltage, and, a negative voltage portion having a minimum voltage, the change from the positive voltage portion to the negative voltage portion occurs within about 0.1 to 0.01 microseconds.

* * * * *